US005824286A

United States Patent [19]

Hodgen

[11] Patent Number: 5,824,286
[45] Date of Patent: Oct. 20, 1998

[54] MAMMOGRAPHY METHOD

[75] Inventor: Gary D. Hodgen, Norfolk, Va.

[73] Assignee: The Medical College of Hampton Roads, Norfolk, Va.

[21] Appl. No.: 464,048

[22] Filed: Jun. 5, 1995

Related U.S. Application Data

[63] Continuation-in-part of Ser. No. 233,696, Apr. 26, 1994, abandoned.

[51] Int. Cl.$^6$ ............................ A61K 31/00; A61K 49/00
[52] U.S. Cl. .............................................. 424/9.1; 435/7.23
[58] Field of Search .............................. 424/9.1; 435/7.23

[56] References Cited

U.S. PATENT DOCUMENTS 5,340,585   8/1994   Pike .

FOREIGN PATENT DOCUMENTS 9119743   12/1991   WIPO .

OTHER PUBLICATIONS

Hogden, Keio J. Med 40(1) 25–31, 1991.
Leal, Drugs of the Future 16(6):529–537, 1991.
Rivier, J. Med. Chem 35:4270–4278, 1992.

Primary Examiner—Toni R. Scheiner
Assistant Examiner—Nancy A. Johnson
Attorney, Agent, or Firm—Ostrolenk, Faber, Gerb & Soffen, LLP

[57] ABSTRACT

The diagnostic interpretation of mammographic films is enhanced by administering to the women undergoing the procedure an effective amount of a gonadotropin releasing hormone antagonist or other inhibitor of ovarian steroid production or action on the breast thereof and effecting the mammogram before the effect of the antagonist or other inhibitor has dissipated.

9 Claims, No Drawings

MAMMOGRAPHY METHOD

BACKGROUND OF THE INVENTION

This is a continuation-in-part of application Ser. No. 08/233,696, filed Apr. 26, 1994 and now abandoned.

There has been considerable debate about the value of mammograms for premenopausal women, particularly those whose age is between 35 and 50 years. It has been estimated that mammography misses about 40% of breast cancers in these premenopausal women because the threshold of sensitivity of mammography is decreased significantly by fibrous tissues and cystic ductal elements of the breasts. These dense tissue structures, along with edematous filling of stromal and ductal regions often cloud the radiologic film. In many younger women, a "negative" mammogram has meant a false sense of security about the absence of early breast disease and leads these women to be less vigilant about doing regular breast examinations.

It is known that the human breast undergoes profound histologic changes corresponding to the phases of the ovarian and menstrual cycles. See, e.g., Fanger et al., Cyclic Changes of Human Mammary Gland Epithelium in Relation to the Menstrual Cycle and Ultrastructural Study, Cancer 34:574–85 (1974); and Vogel et al., The Correlation of Histologic Changes in the Human Breast With the Menstrual Cycle, Mam J. Pathol. 1981 104:23–34.

Peck et al., Estrogen and Post-Menopausal Breast—Mammographic Considerations, Jama, 240:1733–35, 1978, reported on the effect of post-menopausal estrogen replacement therapy on mammographic studies. They noted that estrogen maintained the breast tissue, so that in the post-menopausal women the breast remained firm and the dense breast tissue could obscure a small cancer that otherwise could be palpitated or detected by mammography. Studies withdrawing the hormone replacement therapy for six months or more lead the authors to suggest that malignant neoplasm could be easier to demonstrate if the women of this high risk group did not receive exogenous estrogens.

In the Journal of the Canadian Association of Radiologists, 32:159, 1981, Ouimet-Oliva et al. described a study carried out with 25 women ranging in age from 22 to 47 years afflicted with severe mammary dysplasia. The women were given 400 milligrams per day of danazol (17-alpha-pregna-2,4-dien-20-yno(2,3-d)-isoxazol-17-ol), a synthetic androgen derived from ethisterone. After three months of treatment, the volume and density of the breast had decreased in 80% of the patients and at the end of the treatment, 23 of the 25 patients showed further regression in volume and especially in density such that the entire texture of the breast became exposed. However, danazol has many androgenic side effects. In addition to vasomotor flush of estrogen deprivation, it causes weight gain, long muscle cramps, breast atrophy, hot flashes, mood swings, oily skin, depression, edema, acne, fatigue, hirsutism, alterations in the libido, headache, rash, and a deepening of the voice. Therefore, while such a course of therapy may be tolerable for women afflicted with severe mammary dysplasia, typically it is not practical for other women, especially premenopausal women undergoing a once a year mammography screening.

It is accordingly the object of the present invention to provide a method for enhancing the mammographic films so as to facilitate the analysis of those films by the radiologist in their search for early identifications of either neoplasms or benign cysts. This and other objects of the invention would become apparent to those of ordinary skill in this from the following detailed description.

SUMMARY OF THE INVENTION

This invention relates to enhancing the readability of a mammogram and more particularly to enhancing the readability by administering to the premenopausal women prior to conducting the mammographic procedure a gonadotropin releasing hormone antagonist or mime thereof and then conducting the mammographic procedure before the effect of the gonadotropin releasing hormone antagonist has dissipated.

DESCRIPTION OF THE INVENTION

In accordance with the present invention, the conventional mammographic procedure is carried out but the readability of the radiologic film is enhanced by administering a gonadotropin releasing hormone antagonist or other inhibitor of ovarian steroidal supply impact on breast tissue ("mime") thereof to the women before that procedure is effected.

The gonadotropin releasing hormone is a small polypeptide produced in the hypothalamus and is sometimes termed gonadotropic releasing hormone, luteinizing hormone releasing hormone, GnRH or LHRH. Analogs in the form of antagonists and agonists are known. The present invention employs only the gonadotropin releasing hormone antagonist. A GnRH antagonist acts by classical competitive receptor occupancy at the level of the GnRH receptor in the anterior pituitary. The effect is realized quickly and the more active antagonists can extinguish bioactive gonadotropin secretion within minutes, and in turn deplete gonadal estrogen, progesterone and androgen synthesis and secretion to castrate levels within the first day of treatment without a "flare effect" (stimulation of the receptor system), and in turn, without a delay in therapeutic benefit and without a transient exacerbation by temporary elevations of estrogen and androgen.

Examples of gonadotropin releasing hormone antagonists can be found, iter alia, in U.S. Pat. Nos. 4,409,208, 4,547,370, 4,565,804, 4,569,927, 4,619,914, and 5,198,533 and in WO 89/01944, the disclosures of which are incorporated herein by reference. Examples of such antagonists include Antide (a decapeptide represented by the formula D-Ac-D-2-Nal$^1$-DpClPhe$^2$-D-3-Pal$^3$-Ser$^4$-NiLys$^5$-D-NicLys$^6$-Leu$^7$-ILys$^8$-Pro$^9$-D-Ala$^{10}$), [Ac-D4ClDPhe$^1$, D4ClDPhe$^2$, DTrp$^3$, DArg$^6$, DAla$^{10}$] GnRH, [Ac-4ClDPhe$^2$, D$_3$Pal$^3$, Arg$^5$, D$_2$Nal$^6$, DAla$^{10}$] GnRH, [Ac-D2-Nal$^1$, 4ClDPhe$^2$, DTrp$^3$, DArg$^6$, DAla$^{10}$] GnRH, [Ac-D$_2$Nal$^1$, 4FDPhe$^2$, DTrp$^3$, DArg$^6$] GnRH, [Ac-D2Nal$^1$, 4ClDPhe$^2$, DTrp$^3$, DhArg(Et$_2$)$^6$, DAla$^{10}$] GnRH, and [Ac-Nal$^1$, DME4ClPhe$^2$, DPal$^3$, Ser$^4$, Tyr$^5$, DArg$^6$, Leu$^7$, ILys$^8$, Pro$^9$, DAla$^{10}$] GnRH.

Alternatively, a substitute for the gonadotropin releasing hormone antagonist can be employed. The inhibitors of steroid production or action are entities which mimic the activity of the antagonist sufficiently to reversibly inactivate gonadal response or impact of ovarian steroids on breast tissue, including the blockade of gonadotropin stimulated steroidogenesis. Examples include recombinant DNA derived gonadotropins, desialated gonadotropins whether natural or DNA derived, antibodies to gonadotropins, gonadotropic subunit parts, inhibitors of gonadotropin receptor activations (i.e., cell messengers), inhibin/activin and their analogs, and the like.

The gonadotropin releasing hormone antagonists or other inhibitors employed in the present invention can be administered in the form of pharmaceutically acceptable non-toxic salts or complexes. The salts include acid addition salts such as for instance hydrochloride, hydrobromide, sulfate, phosphate, nitrate, oxalate, fumarate, gluconate, tannate, maleate, acetate, benzoate, succinate, alginate, malate, ascorbate, tartrate and the like. The complexes can be with metals such as for example zinc, barium, calcium, magnesium, aluminum and the like.

The gonadotropin releasing hormone antagonist or other inhibitor administration aspect of the present invention is similar to the previous use of such antagonists for the treatment of endometriosis and/or uterine leiomyomata. Thus not only any known antagonist or inhibitor can be employed, but also the mode of administration heretofore employed can also be employed in the practice of the present invention. Thus, the route of administration can be any conventional route where the analog is active, for instance orally, intravenously, subcutaneously, intramuscularly, sublingually, percutaneously, rectally, intranasally or intravaginally. Similarly, the administration form can be a tablet, dragee, capsule, pill, nasal mist, aerosol, solutions suspensions, suppositories and the like.

As a rule of thumb, the amount of gonadotropin releasing hormone antagonist or inhibitor administered is that sufficient to adjust the circulating estrogen to a value below about 20 pg/ml and preferably below about 10 pg/ml. Depending on the particular active agent employed, the dose administered is generally about 0.001 to 5 mg/kg, preferably about 0.05 to 5 mg/kg when administered intramuscularly. Also depending upon the particular agent employed, a single administration may suffice, although one or more additional administrations can be employed over a time period of about one week or up to 30 days, including daily, weekly or monthly. Since the effects of the administration last for several days, it is preferred that the or the initial gonadotropin releasing hormone antagonist or mime administration occur approximately 7 to 10 days before the mammogram. The depletion of the circulating estrogen causes a transitory thinning of the breast tissue and possible relief of edema. Accordingly, the mammogram is carried out in conventional fashion before endogenous estrogen or progesterone production has been restored spontaneously and causes the breast to revert to its preadministration condition.

In order to demonstrate the present invention, women are first given a mammogram and thereafter administered the gonadotropin releasing hormone antagonist specified below intramuscularly or subcutaneously. One week later the mammogram is repeated resulting in a film which is clearer and easier to interpret in the diagnosis of breast cancer or benign breast lesions. The antagonist and amount which is administered after suspension in sesame oil are:

| Antagonist | Dose mg/kg/day |
|---|---|
| Antide | 0.3 |
| Azaline B | 0.05 |

| Antagonist | Dose mg/kg/day |
|---|---|
| [Ac-D4ClDPhe$^1$, D4ClDPhe$^2$, DTrp$^3$, DArg$^6$, DAla$^{10}$] GnRH | 0.5 |
| [Ac-4ClDPhe$^2$, D$_3$Pal$^3$, Arg$^5$, D$_2$Nal$^6$, DAla$^{10}$] GnRH | 0.5 |
| [Ac-D2-Nal$^1$, 4ClDPhe$^2$, DTrp$^3$, DArg$^6$, DAla$^{10}$] GnRH | 0.5 |
| [Ac-Nal$^1$, DME4ClPhe$^2$, DPal$^3$, Ser$^4$, Tyr$^5$, DArg$^6$ Leu$^7$, ILys$^8$, Pro$^9$, DAla$^{10}$] GnRH | 0.5 |

Application of the components, compositions and methods of this invention for the medical and/or pharmaceutical use which are described in this text may be accomplished by any clinical, medical or pharmaceutical methods or techniques as are presently or prospectively known to those skilled in the art. The various embodiments which have been described herein were intended to be representative and not limiting, as various changes and modifications can be made in the present invention without departing from the spirit and scope thereof.

What is claimed is:

1. A mammographic method in which the image on the mammographic film has enhanced readability relative to a mammogram effected in the absence of the method, comprising the steps of administering to a premenopausal women an agent consisting essentially of an amount of a gonadotropin releasing hormone antagonist or mime thereof effective to deplete circulating estrogen and effecting a mammogram before said depletion effect of the antagonist or mime thereof having a gonadotropin releasing hormone antagonist activity has dissipated, wherein said administration is a single or multiple dose and wherein the time from initial agent administration to the mammogram does not exceed about 10 days.

2. The method of claim 1 wherein an antagonist is administered.

3. The method of claim 2 wherein the antagonist is administered about 7 to 10 days before the mammogram.

4. The method of claim 3 wherein said administration of the antagonist is a single administration.

5. The method of claim 2 wherein said administration of the antagonist is a single administration.

6. The method of claim 2 wherein about 0.001 to 5 mg/kg of the antagonist is administrated.

7. The method of claim 2 wherein about 0.5 to 5 mg/kg of the antagonist is administrated.

8. The method of claim 2 wherein the antagonist is antide.

9. The method of claim 2 wherein the antagonist is azaline B.

* * * * *